US006186952B1

(12) United States Patent
White et al.

(10) Patent No.: US 6,186,952 B1
(45) Date of Patent: Feb. 13, 2001

(54) MACHINED TILT TRANSDUCER AND METHODS OF MAKING

(75) Inventors: David A. White, San Jose; Donald S. Mamayek, Mountain View; Richard A. Bautista, Palo Alto, all of CA (US)

(73) Assignee: SciMed Life Systems, Inc., Maple Grove, MN (US)

(*) Notice: Under 35 U.S.C. 154(b), the term of this patent shall be extended for 0 days.

(21) Appl. No.: 09/477,202

(22) Filed: Jan. 4, 2000

Related U.S. Application Data

(62) Division of application No. 09/178,010, filed on Oct. 23, 1998, now Pat. No. 6,036,648.

(51) Int. Cl.[7] .................................................. A61B 8/12
(52) U.S. Cl. ................................. 600/459; 29/25.35
(58) Field of Search ..................... 29/25.35; 310/334, 310/367; 600/459

(56) References Cited

U.S. PATENT DOCUMENTS

| | | |
|---|---|---|
| 4,155,259 | 5/1979 | Engeler . |
| 4,482,834 | 11/1984 | Dias et al. . |
| 5,108,411 | 4/1992 | McKenzie . |
| 5,368,035 | 11/1994 | Hamm et al. . |
| 5,429,136 | 7/1995 | Milo . |
| 5,454,373 | 10/1995 | Koger et al. . |
| 5,511,296 * | 4/1996 | Dias et al. ............................ 29/25.35 |
| 5,655,538 * | 8/1997 | Lorraine et al. ..................... 29/25.35 |
| 5,701,901 | 12/1997 | Lum et al. . |
| 5,774,960 * | 7/1998 | De Fraguier et al. ............... 29/25.35 |
| 5,852,860 * | 12/1998 | Lorraine et al. ..................... 29/25.35 |
| 5,877,703 | 3/1999 | Bloss, Jr. . |

FOREIGN PATENT DOCUMENTS

WO 99/39641   8/1999   (WO) .

* cited by examiner

*Primary Examiner*—Marvin M. Lateef
*Assistant Examiner*—Ali M. Imam
(74) *Attorney, Agent, or Firm*—Townsend and Townsend and Crew, LLP

(57) ABSTRACT

In one embodiment, an ultrasound imaging assembly (80) includes a housing (82) having a longitudinal axis (88), a proximal end (86), and a distal ending (84) defining a receptacle (90). The imaging assembly includes a transducer package (60) having a central axis (62) and an imaging surface (66) positioned at a desired angle (106) relative to the central axis. The transducer package is at least partially disposed within the receptacle so that the central axis is generally perpendicular to the longitudinal axis. Such a configuration permits a relatively large percentage of the ultrasound signal to pass through a sheath (120) surrounding the imaging assembly and reduces assembly-to-assembly variations.

19 Claims, 7 Drawing Sheets

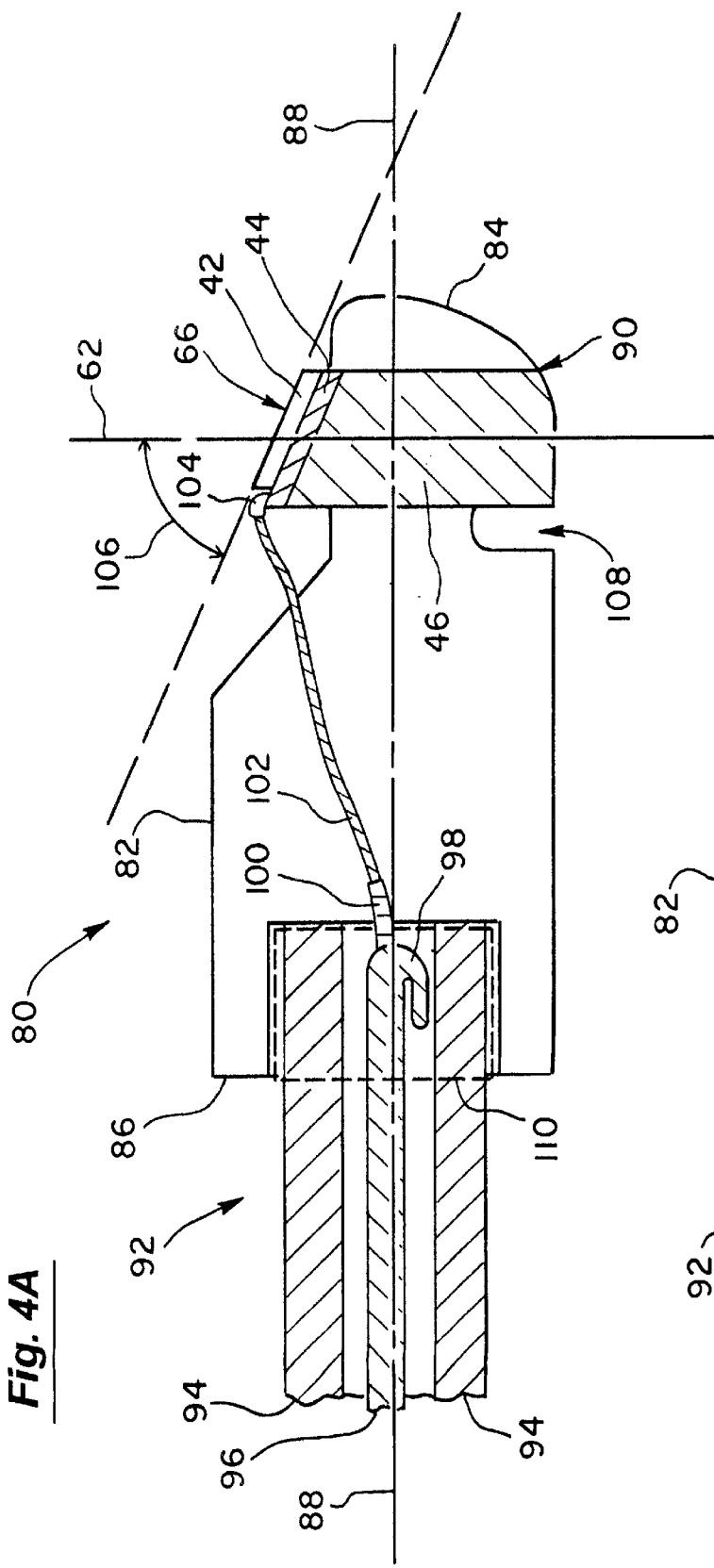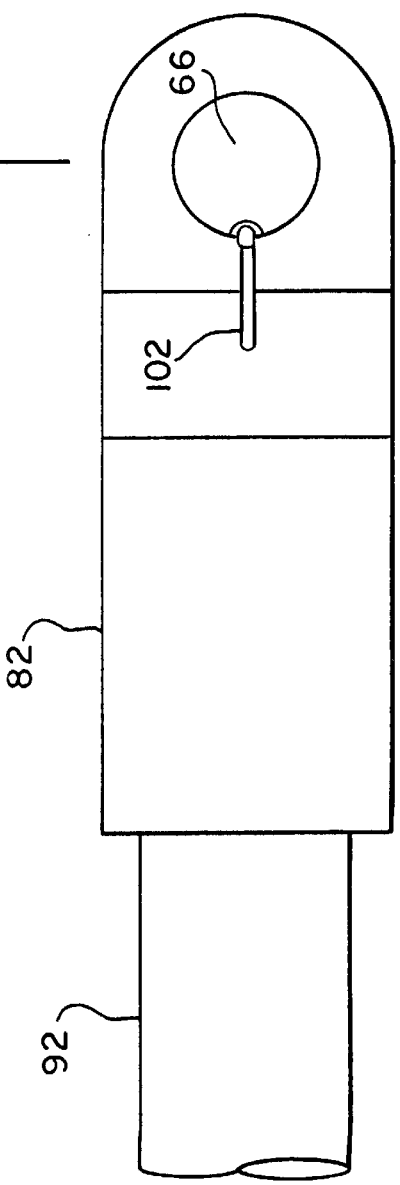

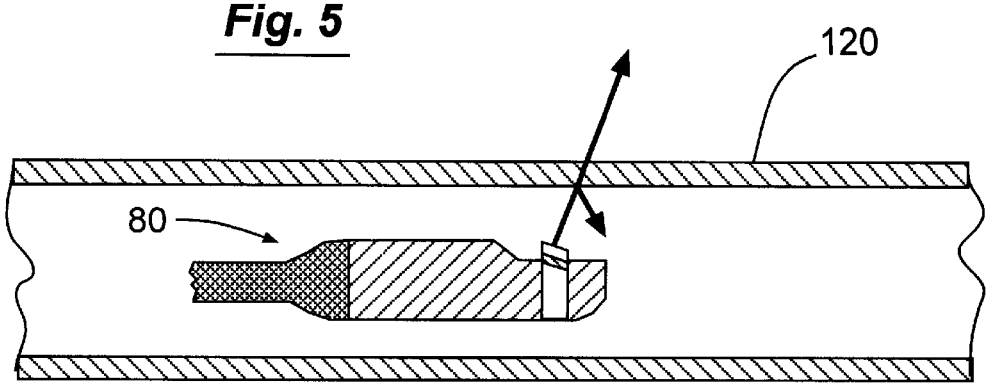
*Fig. 5*
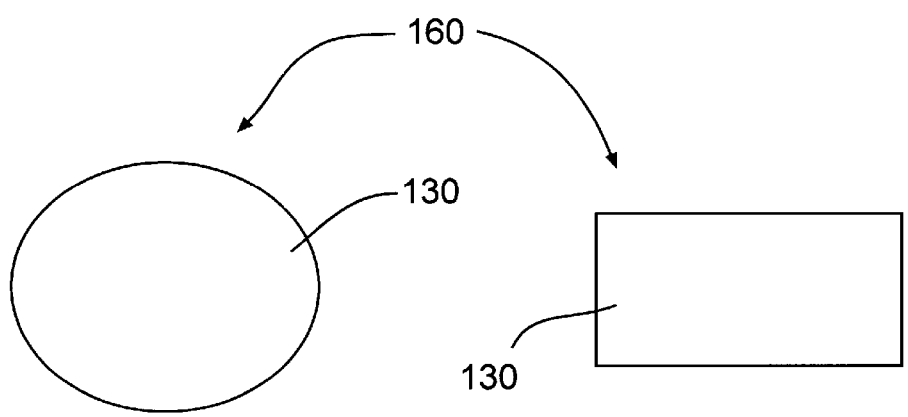
*Fig. 6A*
*Fig. 6B*
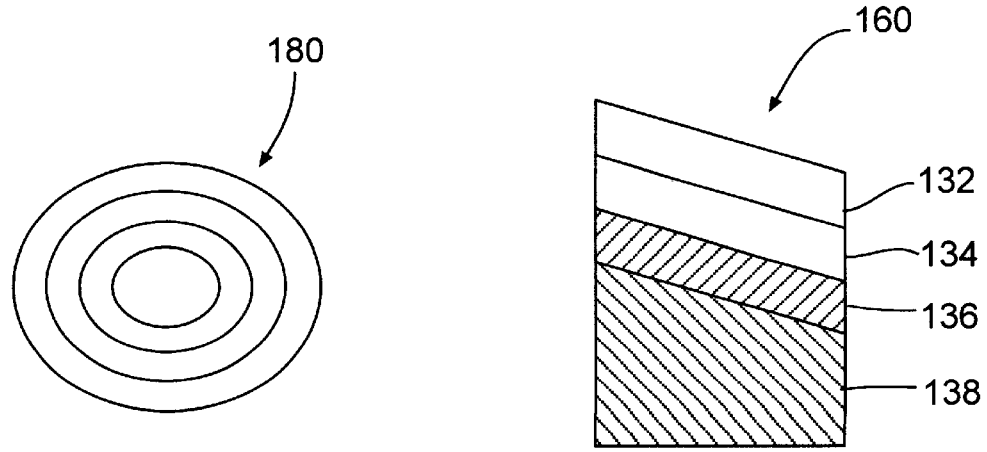
*Fig. 6C*
*Fig. 6D*

MACHINED TILT TRANSDUCER AND METHODS OF MAKING

This application is a divisional of and claims priority of U.S. Pat. application No. 09/178,010, filed Oct. 23, 1998, now U.S. Pat. No. 6,036,648 the disclosure of which is incorporated herein by reference.

BACKGROUND OF THE INVENTION

The present invention relates generally to ultrasonic imaging catheters, and more particularly, to improved ultrasound imaging assemblies and methods of making same.

Intravascular imaging of blood vessels and surrounding tissues continues to be of great benefit in a wide range of medical fields. A particularly successful design for an intravascular imaging catheter is shown in FIG. 1. The catheter 10 employs a rotatable imaging assembly 12 containing an ultrasound transducer 14, where the assembly is attached to the distal end of a flexible drive cable. A flexible sheath 18 is inserted into a patient, and the drive cable and imaging assembly are inserted into the sheath. The transducer may be rotated in order to transmit an ultrasound signal and produce a video image by well-known techniques.

To produce images, it is desirable to have ultrasound signals 20 transmitted by the transducer pass through the sheath (as shown by arrow 22) and reflect off of tissue or fluids. However, a portion of the ultrasound signals transmitted by the transducer typically are reflected by the sheath (as shown by arrow 24). The amount of signal reflected typically is greatest when the angle of incidence between the signal and the sheath is about 90 degrees. Hence, as shown in FIG. 1, it is desirable to tilt the transducer relative to the sheath, thereby reducing the amount of reflected signal.

Angling the transducer typically involves forming a hole 16 in the assembly at the desired angle. However, the formation of an angled hole, particularly in such a diminutive assembly, presents difficulties. For example, angled holes typically have irregularities caused by the hole formation technique. The transducers often are placed and affixed by hand, which can lead to variations in transducer alignment between otherwise identical assemblies.

It is desirable, therefore, to provide imaging assemblies with firmly affixed transducers positioned at the proper angle relative to the sheath. It also is desirable to provide imaging assemblies that are easier to manufacture, and have greater consistency from assembly to assembly.

SUMMARY OF THE INVENTION

The present invention provides exemplary ultrasound imaging assemblies and methods of making same. Imaging assembles of the present invention have a machined tilt transducer package to position the transducer at the proper angle, thereby reducing the amount of reflected ultrasound signal from the sheath, and to improve consistency from transducer assembly to transducer assembly.

In one exemplary embodiment of the present invention an ultrasound imaging assembly includes a housing having a distal end, a proximal end, and a longitudinal axis. The distal end defines a receptacle. The imaging assembly includes a transducer package having a central axis and an imaging surface positioned at a desired angle relative to the central axis. The transducer package is at least partially disposed within the receptacle so that the central axis is generally perpendicular to the longitudinal axis. Preferably, the imaging surface is not coaxial with the longitudinal axis. In this manner, the imaging surface is positioned to permit a relatively large percentage of the ultrasound signal to pass through a sheath surrounding the imaging assembly. The use of a transducer package having the central axis positioned generally perpendicular to the housing longitudinal axis further permits the use of receptacles that are generally perpendicular to the longitudinal axis. In this manner, assembly-to-assembly variations are reduced, due in part by eliminating the need to make angled holes in the housing.

In one aspect of the present invention, the imaging surface has a shape that is generally elliptical. In another aspect, the transducer package includes an annular array of transducer elements. It will be appreciated by those skilled in the art that the transducer package may include transducer elements and imaging surfaces having a variety of different shapes within the scope of the present invention.

In one particular aspect, the desired angle between the central axis and the imaging surface is between about 30 degrees and about 150 degrees, and more preferably, between about 75 degrees and about 105 degrees. In this manner, the imaging surface is positioned at the proper angle to permit the transmission of ultrasound signals through the sheath. Further, for a transducer package that has a central axis generally perpendicular to the housing longitudinal axis, the angle between the longitudinal axis and the imaging surface is between about +60 degrees and about −60 degrees.

In one aspect, the housing includes stainless steel and may be plated with an electrically conductive material. The housing may be plated, for example, with gold, silver, gold over nickel over copper, and the like. Preferably, the housing proximal end is adapted to be coupled to a drive cable. In this manner, the imaging assembly may be rotated during operation thereof.

In another aspect, the receptacle is a generally cylindrical shaped receptacle having an inner wall. Preferably, the transducer package is disposed within the receptacle to contact the inner wall. In this manner, tight tolerances can be maintained to help reduce or eliminate unwanted transducer package movements within the receptacle.

In one aspect, the transducer package includes at least one matching layer operably attached to a transducer element. Alternatively, the transducer package includes a transducer element operably attached to and between a matching layer and a backing layer. It will be appreciated by those skilled in the art that a plurality of matching layers, or no matching layer, may be used within the scope of the present invention. In one particular aspect, the backing layer is electrically conductive. Alternatively, the backing layer is electrically nonconductive.

In still another aspect, the imaging assembly further includes a potting well located in the distal end. The potting well is adapted to receive an electrically conductive material so that the material is in contact with the transducer package, and preferably in contact with the backing layer.

The present invention further provides an exemplary ultrasound imaging catheter. The imaging catheter includes an imaging assembly, ostensibly as previous described, and a drive cable coupled to the proximal end.

The invention also provides exemplary methods of making an ultrasound imaging assembly. In one exemplary method, a first transducer package is provided having an imaging surface. A cutting device is provided and the first transducer package is positioned so that the imaging surface is at a desired angle relative to the cutting device. The method includes cutting the first transducer package with the cutting device to form a second transducer package having a central axis. The central axis is at the desired angle relative to the imaging surface. The method includes providing a housing having a distal end, a proximal end and a longitudinal axis, with the distal end defining a receptacle. The second transducer package is positioned to be at least partially disposed within the receptacle so that the central axis is generally perpendicular to the longitudinal axis. In this manner, the second transducer package has a machined angle, thereby permitting use of a receptacle that is generally perpendicular to the longitudinal axis. In one aspect, the desired angle between the central axis and imaging surface is between about 30 degrees and about 150 degrees. Alternatively, the desired angle is between about 75 degrees and about 105 degrees.

In one aspect of the present invention, the cutting device is selected from a group of cutting devices consisting of a cutting blade, a drill such as a core drill, a laser, an end mill, and the like. In another aspect, the receptacle and second transducer package are generally cylindrical. In still another aspect, the second transducer package is generally cylindrical and the imaging surface is generally elliptical.

In one particular aspect, the method includes the step of removing a portion of the matching layer to define an electrical lead attachment point. In one aspect, the lead attachment point is aligned to be a proximal-most point of the second transducer package.

The invention further provides exemplary methods of manufacturing an ultrasound transducer package. One such method includes providing a transducer element having first and second electrodes operably attached to first and second transducer element surfaces. A matching layer is operably attached to the first electrode and a backing material is operably attached to the second electrode. A laser, preferably an excimer laser, is aligned over a desired region of the matching layer to ablate the desired region. In this manner, laser ablation accurately creates a notch so that a lead can be electrically connected to the first electrode.

In one aspect the laser is aligned over a second desired region located in the backing material and operated to ablate the second desired region. In one aspect of the method, the desired region is ablated until the first electrode is visible. Similarly, the laser is operated to ablate the second desired region until the second electrode is visible. In another aspect, the laser is operated for a desired number of pulses at a power level sufficient to ablate the matching layer and insufficient to ablate the first electrode.

Other features and advantages of the invention will appear from the following description in which the preferred embodiment has been set forth in detail in conjunction with the accompanying drawings.

BRIEF DESCRIPTION OF THE DRAWINGS

FIG. 4A is a side cross sectional view of an exemplary imaging catheter according to the present invention;

FIG. 4B is a top overall view of the catheter shown in FIG. 4A;

FIG. 5 is a side cross sectional view of an imaging catheter of the present invention within a sheath;

FIGS. 6A–6C are overall top views of alternative transducer packages according to the present invention;

FIG. 6D depicts a side cross sectional view of another transducer package according to the present invention;

DETAILED DESCRIPTION OF THE PREFERRED EMBODIMENT

Figure 2A:
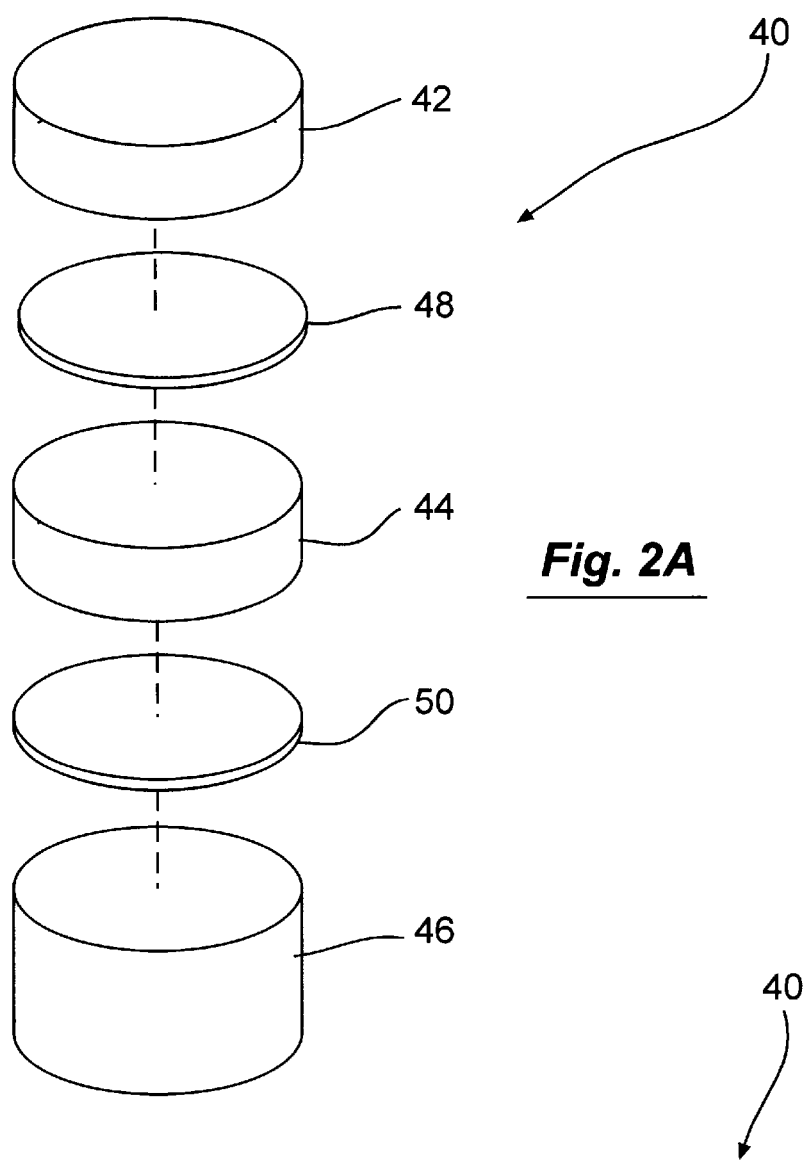
FIGS. 2A–2B depict transducer packages according to the present invention.
Figure 2B:
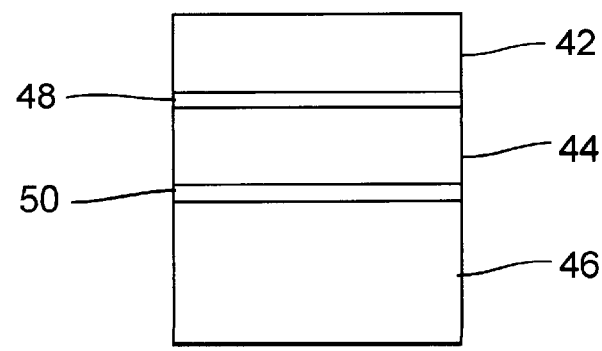

FIGS. 2A–2B depict a first transducer package 40 containing a matching layer 42, a transducer element 44, and a backing material 46. Transducer element 44 may comprise a variety of the materials, including piezocomposite materials, piezoceramics (such as PZT), piezoplastics, and the like. A first electrode 48 and a second electrode 50 are operably attached to opposing sides of transducer element 44. Electrodes 48 and 50 typically cover one entire surface of transducer element 44, as shown in FIG. 2A. However, electrodes 48 and 50 may cover a smaller or greater portion of transducer element 44. Electrodes 48 and 50 preferably include gold, gold over titanium, gold over nickel, gold over chromium, and the like. As shown in FIG. 2B, matching layer 42, transducer element 44 with electrodes 48 and 50, and backing material 46 are operably connected in a stacked configuration using an epoxy or the like. First transducer package 40 then can be manufactured in accordance with the steps described in conjunction with FIG. 3.

Figure 3A:
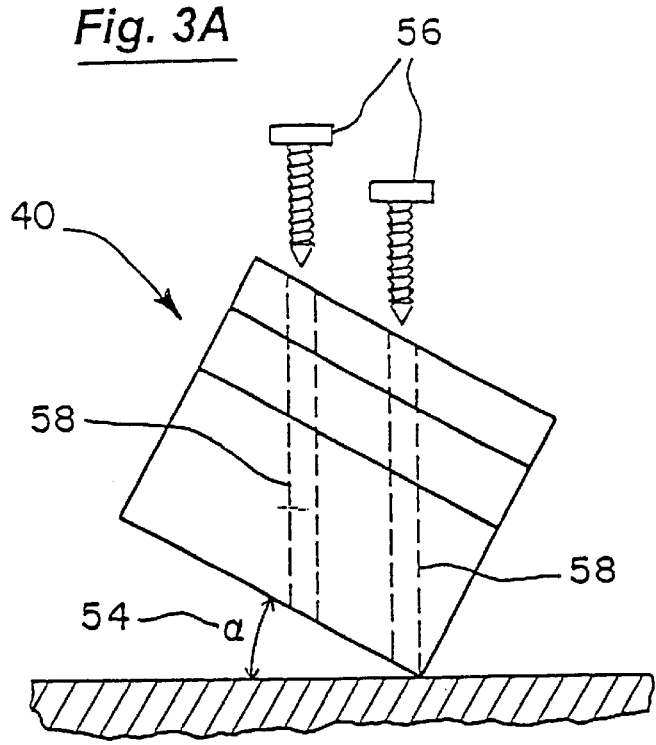
FIGS. 3A–3B depict methods of making transducer packages in accordance with the present invention.

As shown in FIG. 3A, first transducer package 40 is positioned at an angle 54 relative to a cutting device 56. Cutting device 56 may comprise a cutting blade, a drill such as a core drill, a laser, an end mill, and the like. In one particular embodiment, cutting device 56 comprises an end mill having a width of between about 0.010 inch (10 thousandths of an inch) and about 0.050 inch (50 thousandths of an inch). While first transducer package 40 is positioned at angle 54 relative to cutting device 56, cutting device 56 cuts first transducer package 40 along a cut 58 indicated by dashed lines in FIG. 3A. This forms a second transducer package 60 as depicted to FIG. 3B.

Figure 3C:
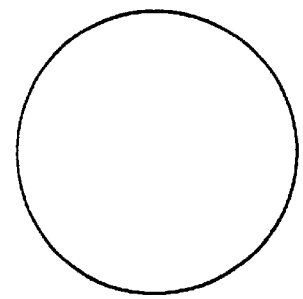
FIGS. 3C–3D are cross-sectional views of the transducer package depicted in FIG. 3B.
Figure 3B:
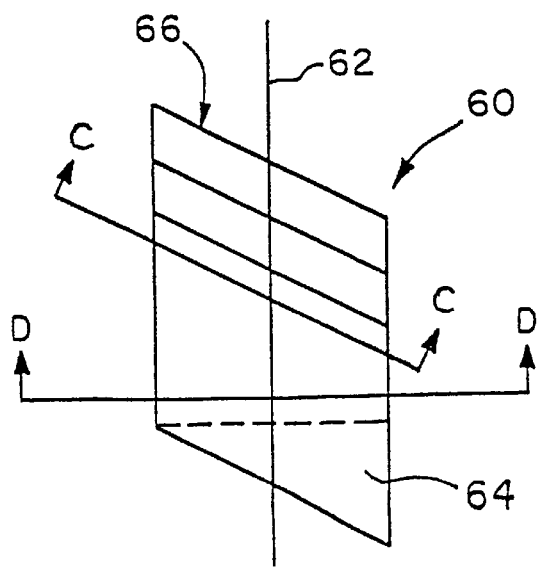
Figure 3D:
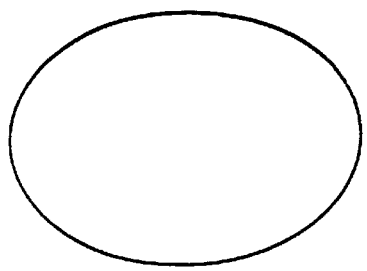

Second transducer package 60 has a central axis 62 and an imaging surface 66. Central axis 62 typically will be coaxial with cut 58 formed by cutting device 56. In the event cutting device 56 is a cylindrical shape cutting device, or is used to provide a cylindrical-shaped cut 58, second transducer package 60 has a cylindrical cross-section as shown in FIG. 3C. Due to angle 54, imaging surface 66 will have an elliptical shape as shown in FIG. 3D. In another embodiment (not shown), second transducer package is formed so that imaging surface 66 has a circular shape. Second transducer package 60 may have an excess portion 64 which can be removed either prior to or after insertion of second transducer package 60 into a housing receptacle as further described in conjunction with FIG. 4.

Turning now to FIGS. 4A–4B, an exemplary imaging assembly configured with an exemplary imaging catheter will be described. FIG. 4A depicts an imaging assembly 80 having a housing 82. Housing 82 has a distal end 84, a proximal end 86, and a longitudinal axis 88. Housing 82 preferably comprises stainless steel plated with an electrically conductive material. For example, housing 82 may be plated with gold, silver, gold over nickel over copper, and the like. Plating housing 82 with electrically conductive material provides housing 82 with an electrically conductive surface which can be used, for example, as a negative or ground connection for transducer element 44. Housing 82 includes a receptacle 90 defined within distal end 84. As shown in FIG. 4A receptacle 90 is filled with second transducer package 60. Prior to or after inserting second transducer package 60 into receptacle 90, excess portion 64 of backing material 46 may be removed to provide distal end 84 with a smooth surface.

Imaging assembly 80 is operably attached to a drive cable 92. Preferably, an epoxy as shown by dashed lines 110 operably attaches drive cable 92 to proximal end 84. In one particular embodiment, drive cable 92 includes a counter-wound 94 surrounding a mini coaxial cable 96. Exemplary drive cables for use with the present invention are further described in U.S. Pat. application Ser. No. 09/017,578 entitled "Integrated Coaxial Transmission Line and Flexible Drive Cable", the disclosure of which is incorporated herein by reference. Mini coaxial cable 96 includes a shield 98 surrounding an insulated lead 100. As shown in FIG. 4A, shield 98 is folded back to reveal insulated lead 100. Insulated lead 100 is striped of insulation to reveal lead 102 which is used as a connection with transducer 44. As shown in FIG. 4A, lead 102 preferably is connected to first electrode 48 by an attachment point 104. Attachment point 104 may comprise electrically conductive epoxy (e.g., silver epoxy) and the like.

As described in conjunction with FIG. 3, second transducer package 60 has been manufactured to position imaging surface 66 at a desired angle relative to central axis 62. Preferably, desired angle 106 as shown in FIG. 4A is between about 30 degrees and about 150 degrees, and more preferably between about 75 degrees and about 105 degrees. In the embodiment shown in FIG. 4A, a potting well 108 is formed in housing distal end 84. Potting well 108 preferably is filled with an electrically conductive material, such as silver epoxy, gold epoxy, conductive silicone, conductive urethane, and the like. In this manner, the conductive material-filled potting well 108 is in contact with backing material 46. For second transducer package 60 having an electrically conductive backing material 46, potting well 108 provides an electrical connection as well as a mechanical connection between backing material 46 and the surface of housing 82. Such a potting well 108 may be necessary to form electrical and mechanical connections due to the tight tolerances between second transducer package 60 and receptacle 90.

As previously indicated, housing 82 preferably is plated with electrically conductive material. By using an electrically conductive epoxy 110 such as silver epoxy or gold epoxy, or conductive silicone, conductive urethane, or the like, an electrically conductive path is established between second electrode 50, backing material 46, conductive material-filled potting well 108, distal housing 82, and shield 98. For the embodiment shown in FIG. 4A, a negative connection is provided to second electrode 50. Lead 102 provides a positive electrical connection to first electrode 48 via attachment point 104. Alternatively the polarities may be reversed within the scope of the present invention.

FIG. 4B depicts a top view of imaging assembly 80. Lead 102 is shown operably attached to the proximal-most portion of transducer 44. In this embodiment, imaging surface 66 is elliptical in shape. It will be appreciated by those skilled in this art, and as shown by way of example in FIG. 6, that a variety of shapes for imaging surface 66 and different locations for attachment point 104 may be used within the scope of the present invention.

As shown is FIG. 5, imaging assembly 80 of the present invention provides imaging surface 66 with the appropriate angle relative to a sheath 120 into which imaging assembly 80 is disposed. In this manner, a large percentage of the ultrasound signal passes through sheath 120 compared to that reflected by sheath 120.

Figure 1:
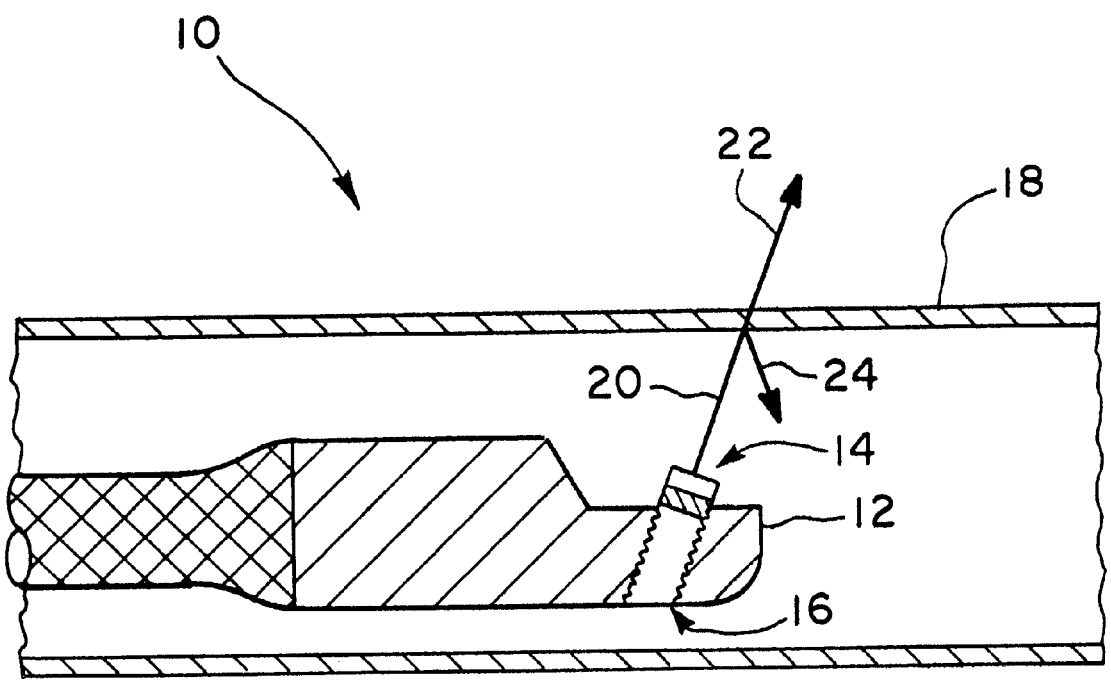
FIG. 1 depicts a typical imaging catheter.

The manufacture of receptacle 90 in distal end 82 also is advantageous. For example, the distal housing shown in FIG. 1 had a saw-tooth configuration due to machining limitations. Machines used to make the distal housing typically have cutting tools that are at right angles with respect to the longitudinal axis of the housing. In order to machine an angled hole, the machinist typically uses an end mill having a smaller cross section than the receptacle cross section. The machinist must step the end mill in and make multiple cuts as the housing is advanced. The resulting angled hole typically is jagged or sawtoothed, and can result in proximal-to-distal movement of the transducer package placed therein.

In contrast, receptacle 90 can be made with a single cut or stroke without producing a jagged or sawtooth receptacle. The cutting device used also can have the same cross section as the desired receptacle 90. The production of a smooth-sided receptacle 90 that is generally perpendicular to housing longitudinal axis 88 can be achieved by a variety of techniques, including drilling, milling, machining, and the like.

Further, by producing desired angle 106 during second transducer package 60 manufacture, increased assembly-to-assembly consistency is achieved, in part by avoiding the need to closely monitor the desired angle while creating receptacle 90 in stainless steel housing 82.

Alternative embodiments of second transducer packages will be described in conjunction with FIG. 6. For example, FIG. 6A depicts a second transducer package 160 having an elliptical imaging surface 130 and FIG. 6B depicts imaging surface 130 as generally rectangular in shape. It will be appreciated by those skilled in the art that a variety of shapes for imaging surface 130 may be used within the scope of the present invention. Further, second transducer package may comprise an annular array 180 of transducer elements as shown in FIG. 6C and as further described in U.S. Pat. application Ser. No. 09/017,581 entitled "Annular Array Ultrasound Catheter", the complete disclosure of which is incorporated herein by reference.

In addition to second transducer package 60 having one matching layer 42 as shown in FIGS. 2–4, it will be appreciated by those skilled in the art that the number of matching layers may vary within the scope of the present invention. For example as shown in FIG. 6D, second transducer package 160 may have first and second matching layers 132 and 134, a transducer element 136 and a backing layer 138.

As shown in FIG. 4, in some embodiments it is desirable to attach lead 102 to first electrode 48 to permit the transmission of electrical signals to and from transducer element 44. As described in conjunction with FIGS. 7 and 8, the present invention provides exemplary methods of creating a notch 140 for lead 102 to use to attach to first electrode 48.

Figure 7A:
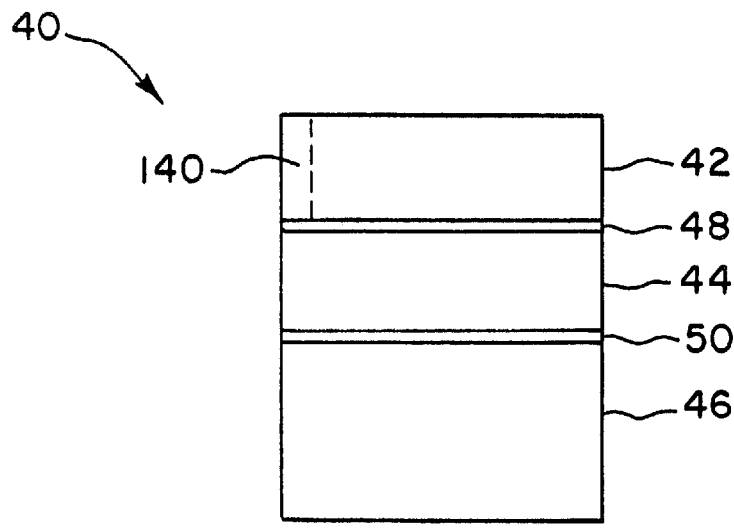
FIGS. 7A–7B depict a notch formed in the transducer package to permit electrical lead attachment to the electrode.
Figure 7B:
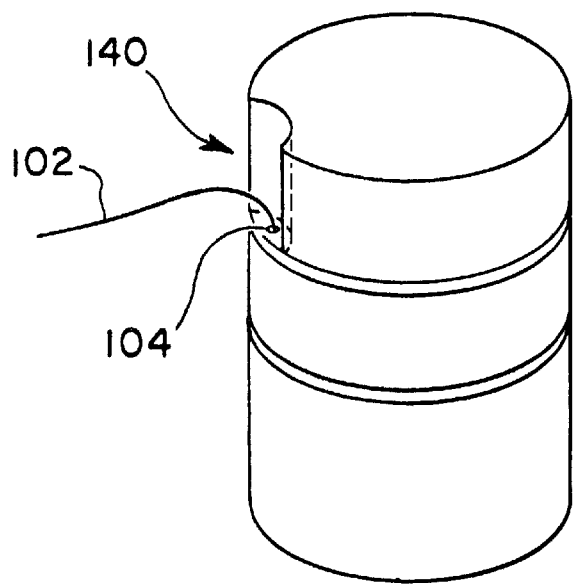
Figure 7C:
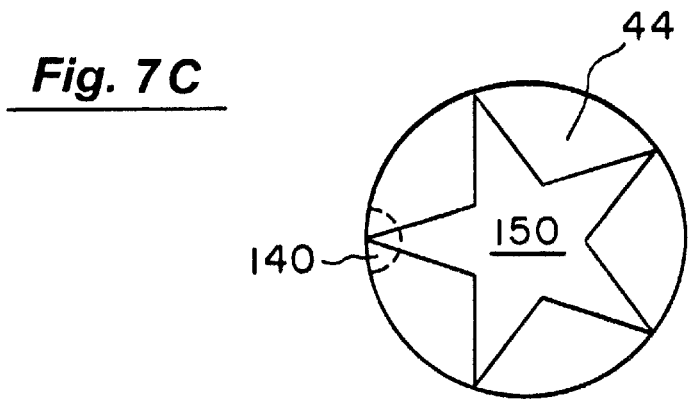
FIG. 7C depicts an alternative electrode for use with the transducer package of the present invention.

FIGS. 7A and 7B depict notch 140 formed in matching layer 42 to permit lead 102 to be attached to first electrode 48 by attachment point 104. While FIGS. 7A–7C depict notch 140 being formed in first transducer package 40, notch 140 also can be formed after manufacture of second transducer package 60 within the scope of the present invention. Further, while notch 140 is depicted formed in a single matching layer 42, notch 140 also can be formed through multiple matching layers for those transducer package embodiments employing more than one matching layer.

Typically, the formation of notch 140 is problematic due in part to the diminutive size of transducer package 40. Further, the creation of notch 140 by hand, such as with a knife or razor blade, can cause variations in notch 140 size between otherwise identical transducer packages 40. Further, in some embodiments it also is desirable to precisely locate notch 140, for example when creating notch 140 to contact a star-shaped electrode 150 as shown in FIG. 7C.

Figure 8:
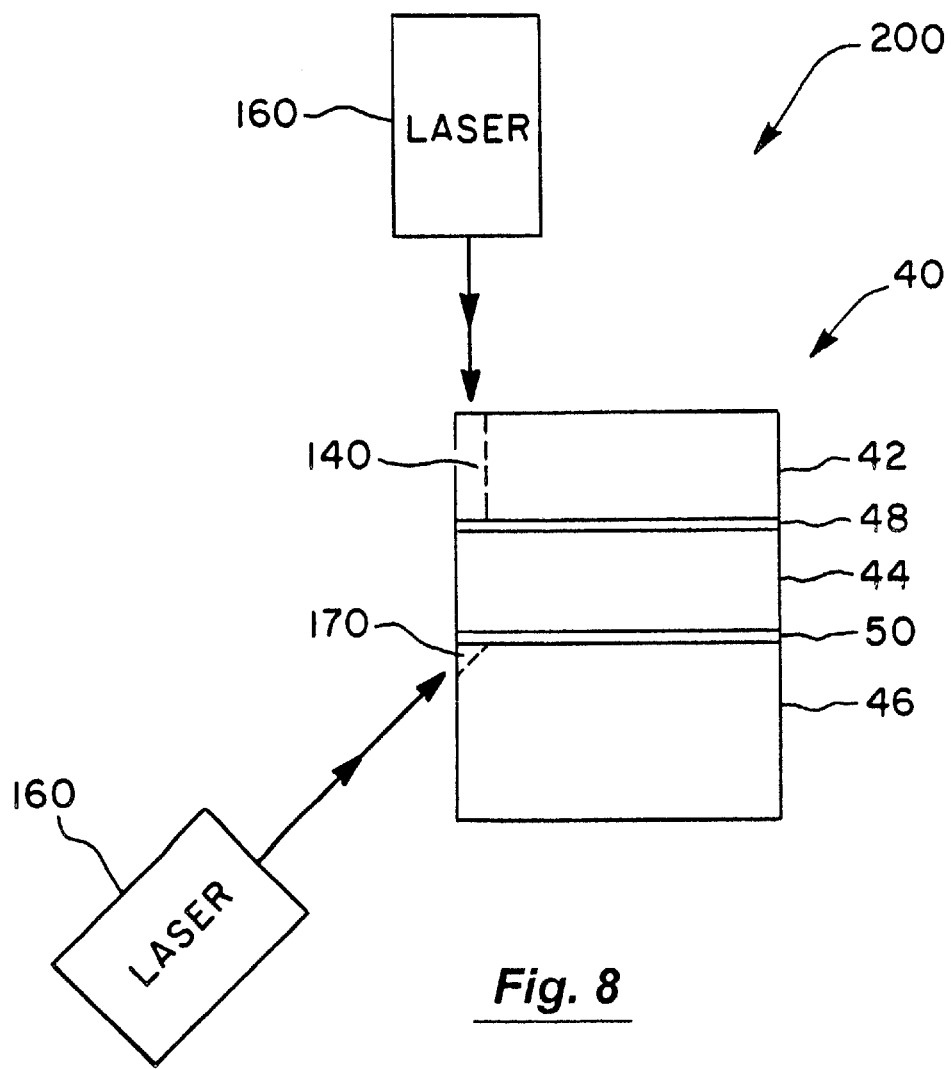
FIG. 8 is a schematic showing laser ablation of notches in the transducer package of FIG. 7.

To overcome at least some of these problems and to precisely create notches 140, the system depicted in FIG. 8 can be used. System 200 uses a laser 160, preferably an excimer laser 160, to create notch 140. Excimer laser 160 operates to dissociate the bonds of the material comprising the matching layer 42. Further, laser 160 can be used to remove the resin or epoxy (not shown) used to affix matching layer 42 to first electrode 48. In this manner, electrode 48 can be exposed to permit lead 102 attachment thereto.

At least part of the present invention involves the recognition that laser ablation can precisely create notch 140 having the desired size. Since matching layer 42 operates to reduce the amount of unwanted ultrasound wave reflection, it is desirable to only remove as much matching layer 42 material as is necessary to permit lead 102 attachment. Operating levels of laser 160 can be set to ablate the appropriate amount of matching layer 42 material to create notch 140 having the desired size. Laser 160 further permits consistency in notch 140 manufacture for a number of transducer packages 40.

Laser 160 also can create notch 140 at a desired location on matching layer 42. In this manner, notch 140 can be used to help correctly align second transducer package in receptacle 90. For example, in the embodiment shown in FIG. 4B, notch 140 is created at the highest point on second transducer package 60. By then positioning second transducer package 60 within receptacle 90 so that notch 140 is the proximal-most point of second transducer package 60, a forward tilt imaging surface 66 can be established.

By way of example, for matching layer 42 comprising silver filled epoxy, other filled epoxies or adhesives, and the like, laser 160 can be operated at about 1.0 Joules/centimeter$^2$ (J/cm$^2$) for about 10 to about 50 pulses of about 0.25 nanoseconds duration to ablate matching layer 42 that is about 0.0003 inches to about 0.007 inches thick. Similarly, energy levels to ablate epoxy connecting matching layer 42 to first electrode 48 are about one to about 1.4 J/cm$^2$. However, the energy levels needed to ablate a metal, such as gold used for first electrode 48 are considerably higher. For example, gold requires about 7 to about 20 J/cm$^2$ to be ablated. Such a difference in ablation energies allows the operation of laser 160 at energy levels sufficient to ensure ablation of matching layer 42 and epoxy, without causing damage to first electrode 48. In this manner, the ablation of matching layer 42 can occur by calculating the number of pulses needed to completely ablate matching layer 42, and operating laser 160 at the required energy levels and pulses. Additional pulses also can be used to ensure complete ablation of matching layer 42, yet occur at power levels low enough to avoid damaging electrode 48. Alternatively, laser 160 can be operated until a visual inspection reveals electrode 48 has been exposed.

Similarly, as shown in FIG. 8, laser 160 can be used to ablate a notch 170 in backing material 46. Notch 170 would be particularly useful in the event backing material 46 is nonconductive. In this manner, notch 170 can be used to provide an electrical contact to electrode 50. It may be desirable to create notch 170 at an angle to minimize the amount of backing material 46 ablated.

It will be appreciated by those skilled in the art that while the present invention has been described with notch 140 formed to expose first electrode 48, alternative methods may be used to mount lead 102 to first electrode 48 within the scope of the present invention. For example, off aperture mounting techniques disclosed in U.S. application Ser. No. 09/127,994, entitled "PZT Off-Aperture Bonding Technique" (Attorney Reference No. 12553-007100), and U.S. application Ser. No. 09/127,089, entitled "Off Aperture Electrical Connection for Ultrasonic Transducer" (Attorney Reference No. 12553-007600) may be used, the complete disclosures of which are incorporated herein by reference.

The invention has now been described in detail. However, it will be appreciated that certain changes and modifications may be made. For example, the use of laser ablation to create notch 140 can be applied to a wide range of transducer configurations, including those described in 09/127,694, entitled "Method of Tuning Ultrasonic Transducer Matching Layer", the complete disclosure of which are incorporated herein by reference. Therefore, the scope and content of this invention are not limited by the foregoing description. Rather, the scope and content are to be defined by the following claims.

What is claimed is:

1. A method of making an ultrasound imaging assembly comprising the steps of:

providing a first transducer package having an imaging surface;

providing a cutting device;

positioning said first transducer package so that said imaging surface is at a desired angle relative to said cutting device;

cutting said first transducer package with said cutting device to form a second transducer package having a central axis, said central axis at said desired angle relative to said imaging surface;

providing a housing having a distal end, a proximal end, and a longitudinal axis, said distal end defining a receptacle; and positioning said second transducer package to be at least partially disposed within said receptacle so that said central axis is generally perpendicular to said longitudinal axis.

2. A method as in claim 1, wherein said first transducer package comprises a transducer element and at least one matching layer.

3. A method as in claim 2, further comprising the step of removing a portion of said matching layer to define an electrical lead attachment point.

4. A method as in claim 3, wherein said positioning the second transducer package step further comprises aligning said electrical lead attachment point to be a proximal-most point of said second transducer package.

5. A method as in claim 1, wherein said first transducer package comprises a transducer element, a matching layer and a backing layer.

6. A method as in claim 1, wherein said cutting device is selected from a group of cutting devices consisting of a cutting blade, a drill, a laser, an end mill, and a core drill.

7. A method as in claim 1, wherein said desired angle is between about 30 degrees and about 150 degrees.

8. A method as in claim 1, wherein said desired angle is between about 75 degrees and about 105 degrees.

9. A method as in claim 1, wherein said receptacle and said second transducer package are generally cylindrical.

10. A method as in claim 1, wherein said second transducer package is generally cylindrical and said imaging surface is generally elliptical.

11. A method of manufacturing an ultrasound transducer package comprising:

provided a transducer element having first and second electrodes operably attached to first and second surfaces of said transducer element, respectively;

operably attaching a matching layer to said first electrode;

operably attaching a backing material to said second electrode;

aligning a laser over a desired region of said matching layer; and ablating said desired region with said laser until a portion of said first electrode is visible.

wherein said ablating comprises operating said laser for a desired number of pulses at a power level sufficient to ablate said matching layer and insufficient to ablate said electrode.

12. A method of manufacturing a transducer package as in claim 11, wherein said aligning comprises aligning an excimer laser.

13. A method of manufacturing a transducer package as in claim 11, further comprising aligning said laser over a second desired region located in said backing material and ablating said second desired region with said laser.

14. A method of manufacturing a transducer package as in claim 13, wherein said ablating said second desired region step comprises ablating said second desired region until a portion of said second electrode is visible.

15. The method as in claim 14 further comprising coupling an electrical lead to said portion of said second electrode.

16. The method as in claim 11 further comprising coupling an electrical lead to said portion of said first electrode.

17. A method of making an ultrasound imaging assembly comprising:

providing a first transducer package having an imaging surface;

providing a cutting device;

positioning said first transducer package so that said imaging surface is at a desired angle relative to said cutting device;

cutting said first transducer package with said cutting device to form a second transducer package having a central axis, said central axis at said desired angle relative to said imaging surface;

providing a housing having a longitudinal axis; and mounting said second transducer package to said housing so that said central axis is generally perpendicular to said longitudinal axis.

18. The method as in claim 17 wherein said first transducer package comprises a transducer element and a matching layer.

19. The method as in claim 17 wherein said first transducer package comprises a transducer element, a matching layer and a backing layer.

* * * * *